Jan. 21, 1964 E. S. BOERNER Plant Pat. 2,347
CHRYSANTHEMUM PLANT
Filed Feb. 4, 1963
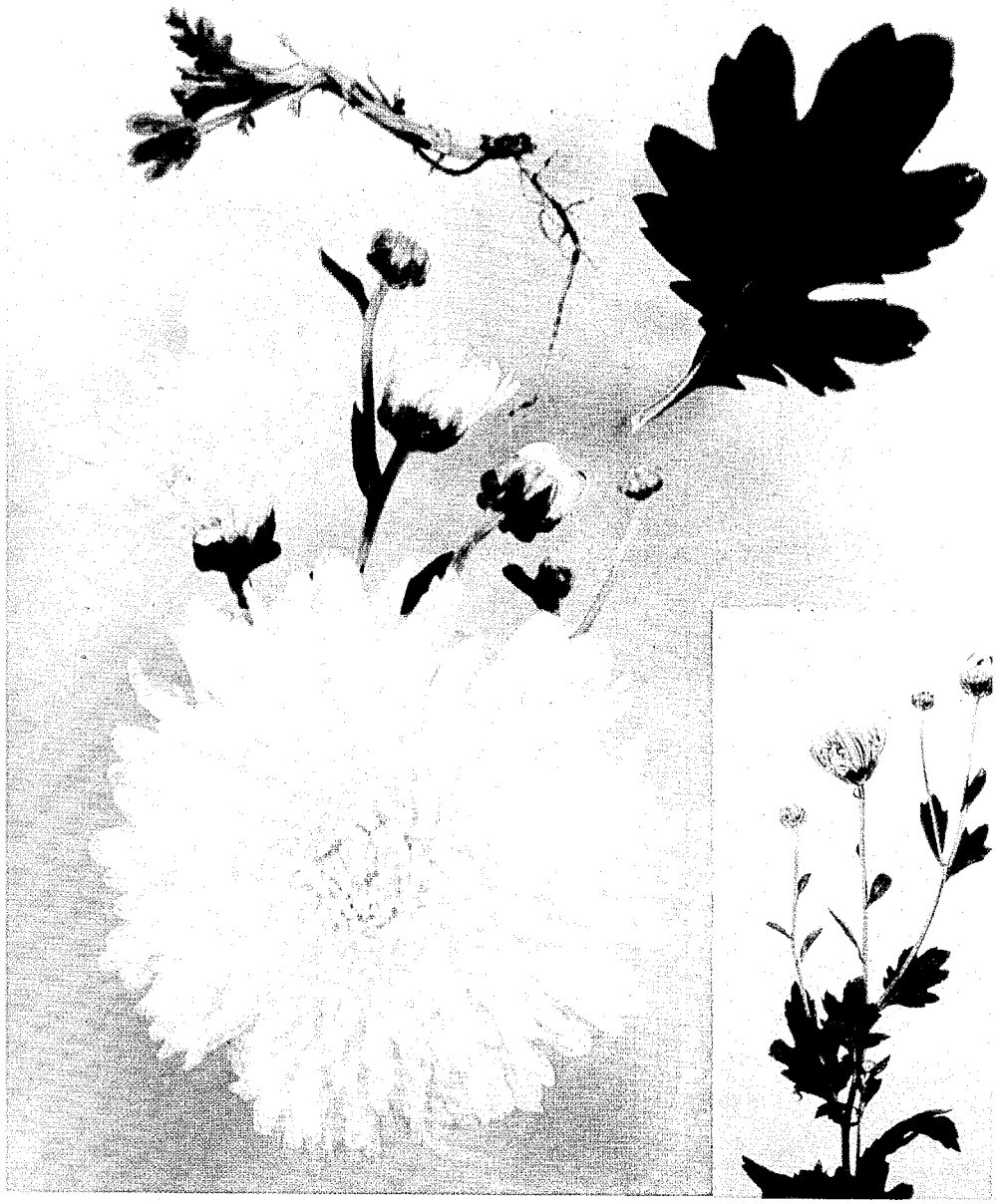
Inventor.
E. S. Boerner
By: Robb & Robb
Attorneys.

United States Patent Office

Plant Pat. 2,347
Patented Jan. 21, 1964

2,347
CHRYSANTHEMUM PLANT

Eugene S. Boerner, Newark, N.Y., assignor to Jackson & Perkins Company, Newark, N.Y., a corporation of New York Filed Feb. 4, 1963, Ser. No. 256,181
1 Claim. (Cl. Plt.—78)

The present invention relates to a new and distinct variety of chrysanthemum plant of the decorative class, which was originated by me by crossing an unnamed and unpatented seedling derived from a cross of "Meadowlark" (Plant Patent No. 1,305) × "Thrush" (Plant Patent No. 1,168) with an unnamed and unpatented Hortorum seedling.

The primary objective of this breeding was to produce a new chrysanthemum variety having the hardiness and vigor of the varieties "Meadowlark" and "Thrush," combined with the large flower size of the unnamed Hortorum seedling parent. This objective was fully achieved, along with other desirable improvements, as evidenced by the following unique combination of characteristics which are outstanding in the new variety and which distinguish it from its parents, as well as from all other varieties of which I am aware:

(1) Hardy and vigorous habits of growth;
(2) Large foliage;
(3) Flowers of large size and exceptional thickness; and
(4) A distinctive and attractive general color tonality of the flowers corresponding to Lemon Chrome, lightly overcast with Lemon Yellow.

Asexual reproduction of the new variety by both top cuttings and underground runners, as performed at Newark, New York, shows that the foregoing characteristics and distinctions come true to form and are established and transmitted through succeeding propagations.

The accompanying drawing shows typical specimens of the vegetative growth and flowers of my new chrysanthemum variety in different stages of development and as depicted in color as nearly true as it is reasonably possible to make the same in a color illustration of this character, as well as a typical specimen stem which is depicted in black-and-white for the purpose of illustrating the form and habit of growth of the stem.

The following is a detailed description of the new variety, with color terminology in accordance with Ridgway's Color Standards and Nomenclature, as based upon observations of specimens grown outdoors at Newark, New York, in the early morning during the latter part of the month of October:

Parentage: Seedling.
*Seed parent.*—An unnamed seedling of "Meadowlark" × "Thrush."

*Pollen parent.*—An unnamed Hortorum seedling.
Classification: Decorative.
Growth: Very free; tall; attains height of about 2½ feet.
Cold resistance: Winter hardy in northern New York State.
Blooming period: From early October until a hard freeze.

*Flower*

Bud:
*Color.*—When sepals first divide—Pale Lemon Yellow, Plate 4. When petals begin to unfurl—Empire Yellow, Plate 4. When half-blown—inside: Lemon Chrome, Plate 4; outside: Pale Lemon Yellow, Plate 4, very lightly overcast with Lemon Chrome, Plate 4.
*Peduncle.* — Color — Biscay Green, Plate 17. Strength—strong.

Bloom:
*Size.*—6 inches in diameter.
*Stem.*—Strong.
*Form.*—Decorative; thick.
*Petalage.*—At least 2½ inches deep.
*Color.*—Center of flower—Lemon Chrome, Plate 4. Outer petals—Pale Lemon Yellow, Plate 4. Base of petals—Chalcedony Yellow, Plate 17. Inside of petals—Lemon Chrome, Plate 4, lightly overcast with Lemon Yellow, Plate 4. Reverse of petals—Pale Lemon Yellow, Plate 4, very lightly overcast with Empire Yellow, Plate 4.
*Petals.*—Texture—thin; smooth. Form—oval.
*Fragrance.*—Characteristic chrysanthemum.

*Plant*

Form: Upright.
Growth: Free.
Foliage:
*Size.*—Large.
*Quantity.*—Normal.
*Color.*—Upper side—Dark Cress Green, Plate 31. Reverse side—Bice Green, Plate 17.
*Texture.*—Leathery.

I claim:

A new and distinct variety of chrysanthemum plant of the decorative class, substantially as herein shown and described, characterized particularly as to novelty by the unique combination of hardy and vigorous habits of growth, large foliage, flowers of large size and exceptional thickness, and a distinctive and attractive general color tonality of the flowers corresponding to Lemon Chrome, lightly overcast with Lemon Yellow.

No references cited.